(12) United States Patent
Jeon et al.

(10) Patent No.: US 10,502,668 B2
(45) Date of Patent: Dec. 10, 2019

(54) METHOD OF COLLECTING TARGET CELLS

(71) Applicant: CYTOGEN CO., LTD., Seongnam-si, Gyeonggi-do (KR)

(72) Inventors: Byung Hee Jeon, Seongnam-si (KR); Jong Kil Lee, Incheon (KR)

(73) Assignee: CYTOGEN CO., LTD., Seongnam-si (KR)

( * ) Notice: Subject to any disclaimer, the term of this patent is extended or adjusted under 35 U.S.C. 154(b) by 0 days.

(21) Appl. No.: 15/150,311

(22) Filed: May 9, 2016

(65) Prior Publication Data

US 2016/0252436 A1 Sep. 1, 2016

Related U.S. Application Data

(63) Continuation of application No. 13/881,692, filed as application No. PCT/KR2011/007977 on Oct. 25, 2011, now abandoned.

(30) Foreign Application Priority Data

Oct. 25, 2010 (KR) ........................ 10-2010-0104251

(51) Int. Cl.
*G01N 1/40* (2006.01)
*C12M 1/00* (2006.01)
(Continued)

(52) U.S. Cl.
CPC ........... *G01N 1/4077* (2013.01); *C12M 47/02* (2013.01); *C12M 47/04* (2013.01); *G01N 1/34* (2013.01);
(Continued)

(58) Field of Classification Search
CPC ........ B01L 61/082; B01L 61/14; B01L 61/18; B01L 2300/0681; C12N 15/1003; G01N 1/34; G01N 33/5002; G01N 2001/4016
(Continued)

(56) References Cited

U.S. PATENT DOCUMENTS

| 3,397,704 A | 8/1968 | Marinaccio |
| 5,043,082 A | 8/1991 | Hermann, Jr. et al. |

(Continued)

FOREIGN PATENT DOCUMENTS

| CN | 101583722 A | 11/2009 |
| JP | 6-500403 A | 1/1994 |

(Continued)

OTHER PUBLICATIONS

Japanese First Office Action dated Sep. 24, 2014 of corresponding Japanese Patent Application No. 2013-536505—3 pages.

(Continued)

*Primary Examiner* — Liban M Hassan
(74) *Attorney, Agent, or Firm* — Novick, Kim & Lee, PLLC; Jae Youn Kim

(57) ABSTRACT

A method of collecting target cells including providing a cell collection device comprising a conduit defining a fluid channel, a first screen and a second screen, the first and second screens are movable relative to each other along the flow direction between a first configuration and a second configuration, flowing a fluid composition comprising the target cells in the flow direction while the first and second screens are in a first configuration to screen at least part of the target cells, moving the first screen relative to the second screen along the flow direction from the first configuration to form the second configuration, to permit at least part of the target cells screened in the first configuration to pass the first screen first and then the second screen, and collecting (Continued)

at least part of the target cells at the second end of the fluid channel.

10 Claims, 10 Drawing Sheets

(51) Int. Cl.
    *G01N 1/34*     (2006.01)
    *B01L 3/00*     (2006.01)

(52) U.S. Cl.
    CPC .. *B01L 3/50255* (2013.01); *G01N 2001/4088* (2013.01)

(58) Field of Classification Search
    USPC ................................ 435/5, 309.1, 345, 308.1
    See application file for complete search history.

(56) References Cited

U.S. PATENT DOCUMENTS

| | | |
|---|---|---|
| 5,139,031 A | 8/1992 | Guirguis |
| 5,489,930 A | 2/1996 | Anderson |
| 5,556,598 A | 9/1996 | Raybuch et al. |
| 6,877,964 B2 * | 4/2005 | Burns ................... B01F 5/0683 137/625.33 |
| 2002/0195386 A1 | 12/2002 | Young et al. |
| 2004/0086390 A1 * | 5/2004 | Burns ................... B01F 5/0683 417/48 |
| 2005/0249917 A1 | 11/2005 | Trentacosta et al. |
| 2007/0025883 A1 | 2/2007 | Tai et al. |
| 2007/0190653 A1 | 8/2007 | Heinrich |
| 2009/0188864 A1 | 7/2009 | Zheng et al. |

FOREIGN PATENT DOCUMENTS

| | | |
|---|---|---|
| JP | 10-137557 A | 5/1998 |
| JP | 2001-116873 A | 4/2001 |
| JP | 2001-513419 A | 9/2001 |
| JP | 2005-138083 A | 6/2005 |
| JP | 2011-510656 A | 4/2011 |
| KR | 20-0399984 Y1 | 11/2005 |
| KR | 10-2009-0079487 A | 7/2009 |
| WO | 2009-097247 A1 | 8/2009 |

OTHER PUBLICATIONS

Japanese Second Office Action dated Aug. 25, 2015 of corresponding Japanese Patent Application No. 2013-536505—4 pages.
Chinese Office Action dated Mar. 26, 2014 of corresponding Chinese Patent Application No. 201180062661.1—7 pages.
International Search Report dated May 21, 2012 of PCT/KR2011/007977 which is the parent application—4 pages.

* cited by examiner

[Fig. 1]
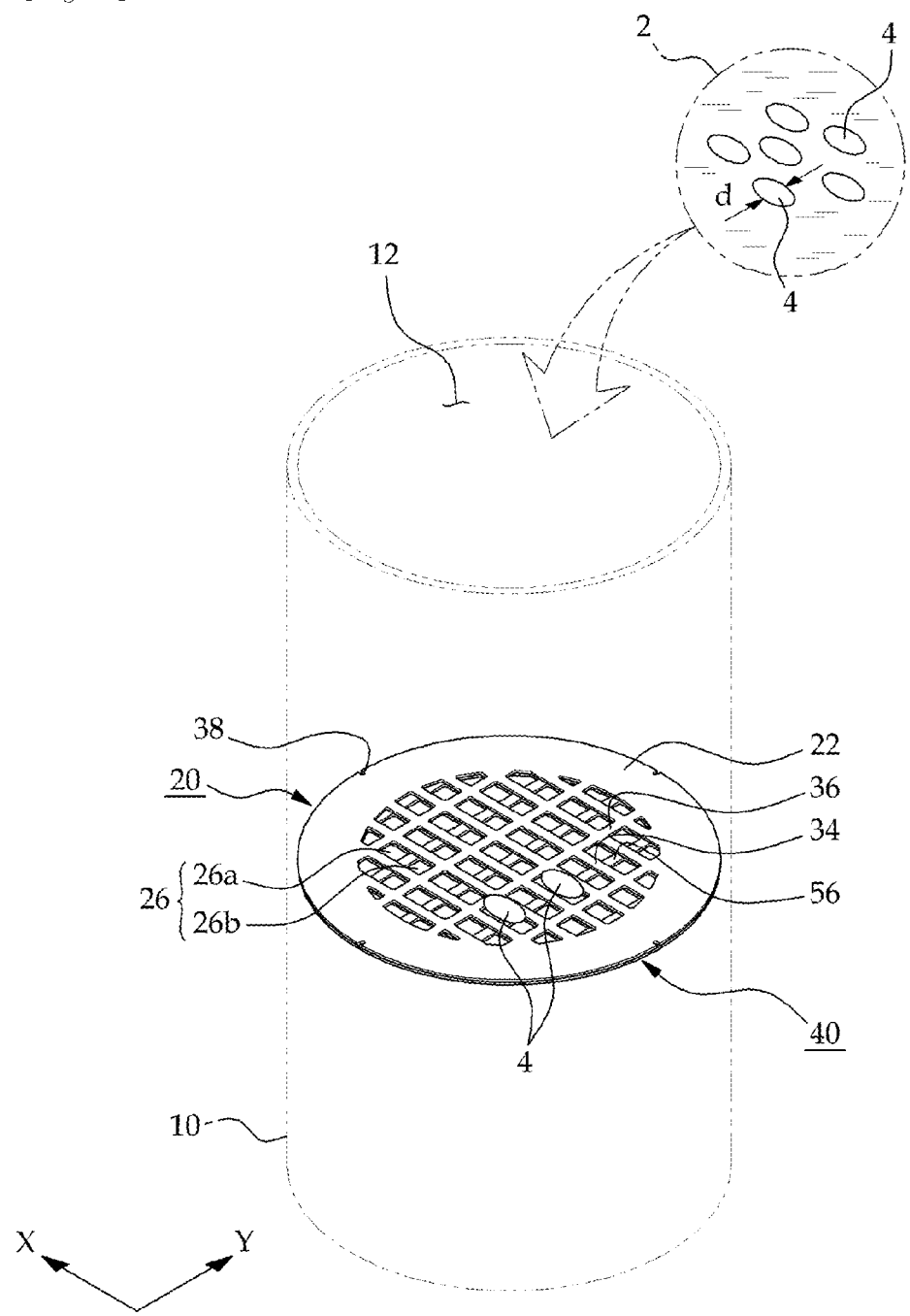

[Fig. 2]
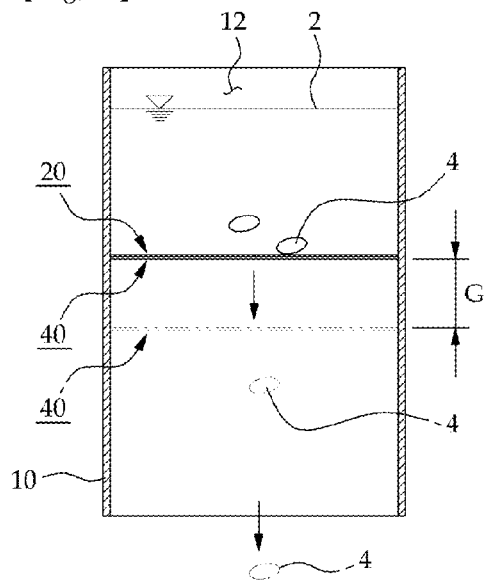
[Fig. 3]
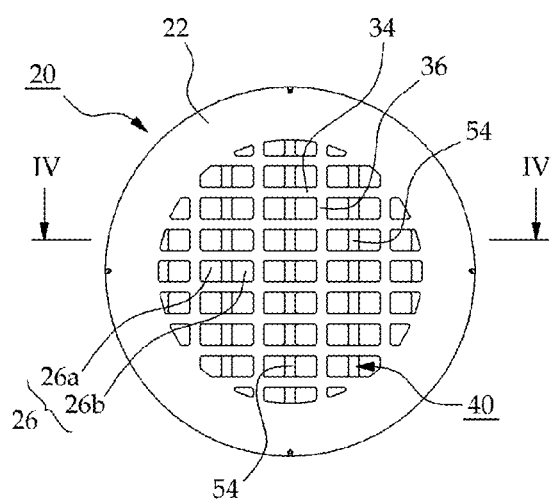
[Fig. 4]
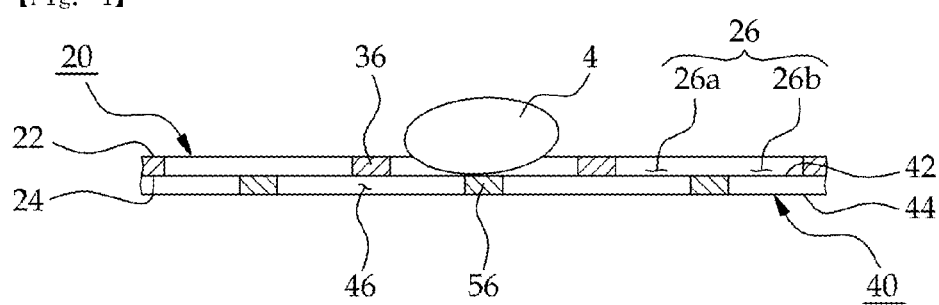

[Fig. 5]
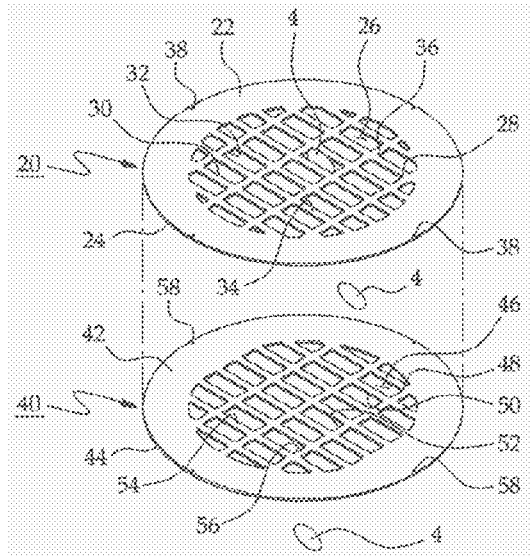
[Fig. 6]
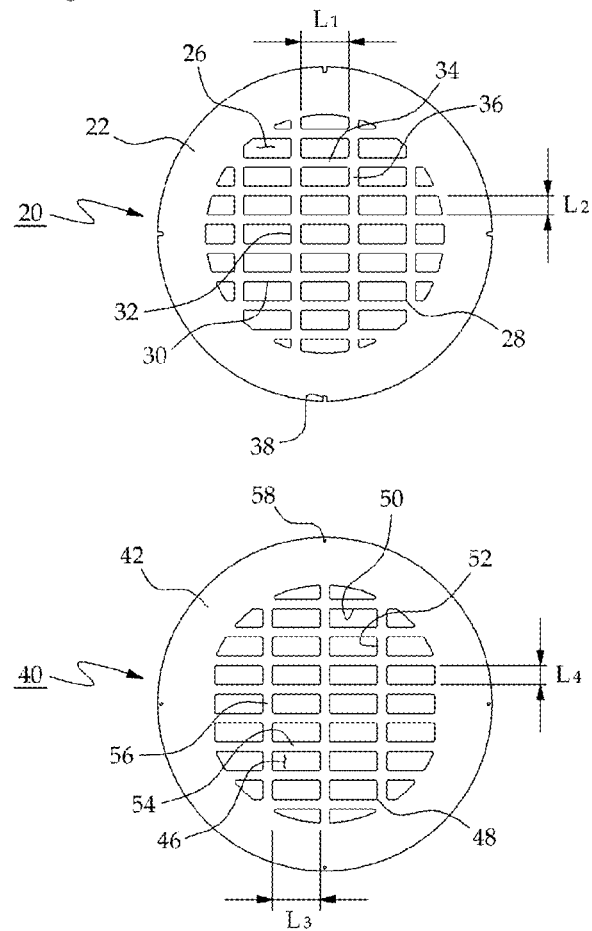

[Fig. 7]
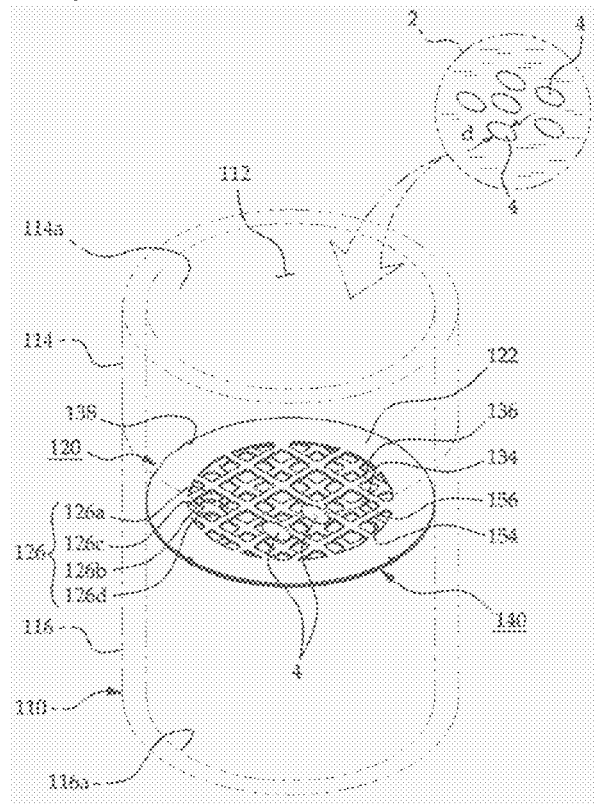
[Fig. 8]
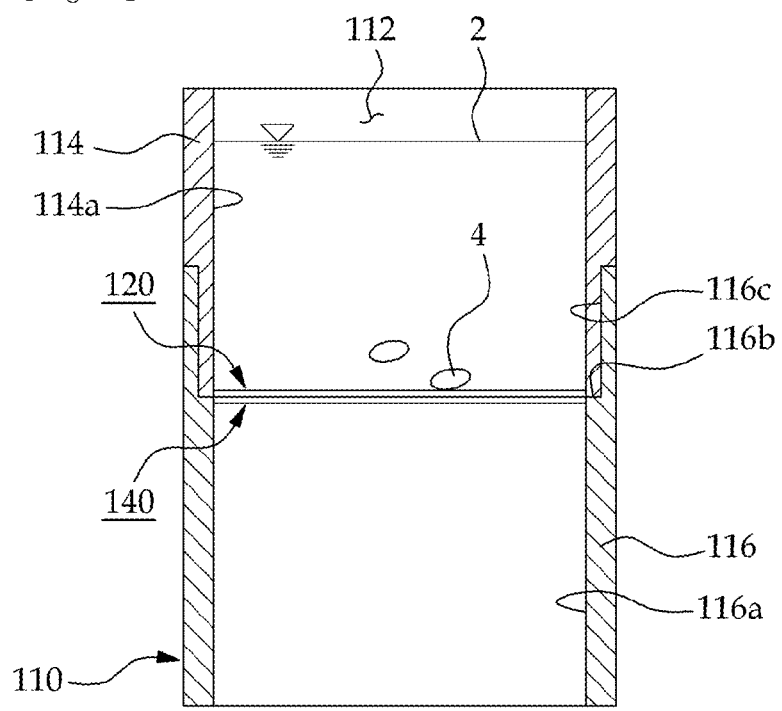

[Fig. 9]
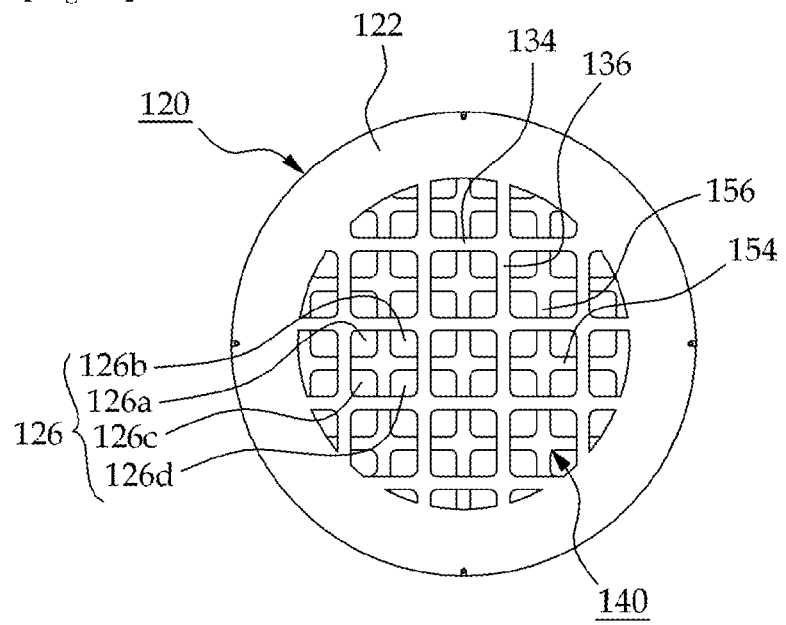
[Fig. 10]
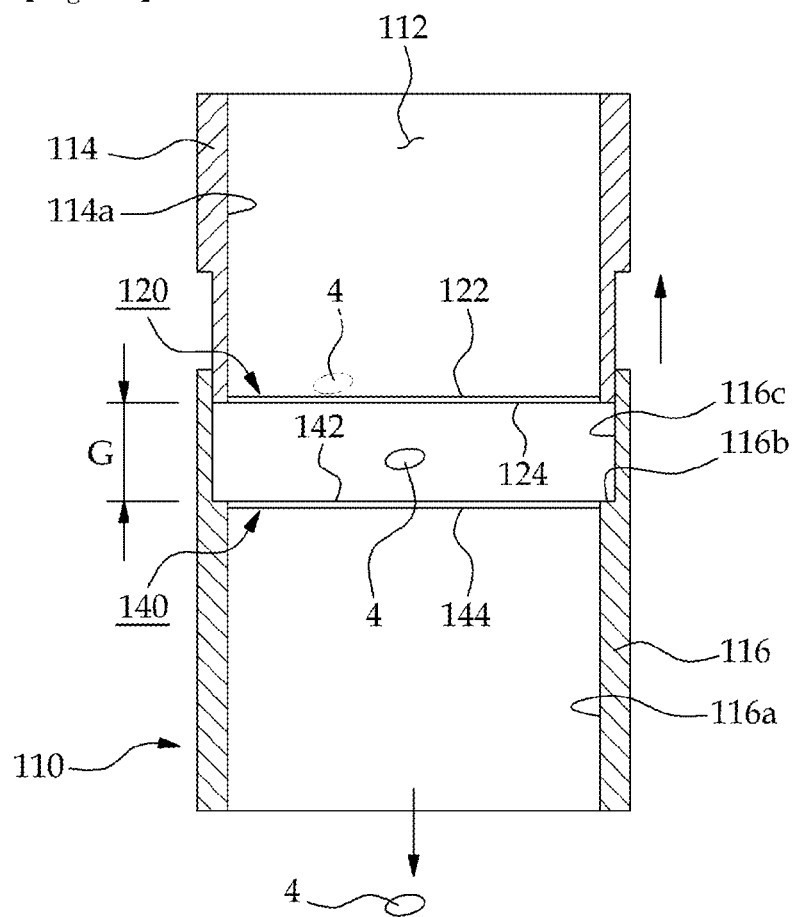

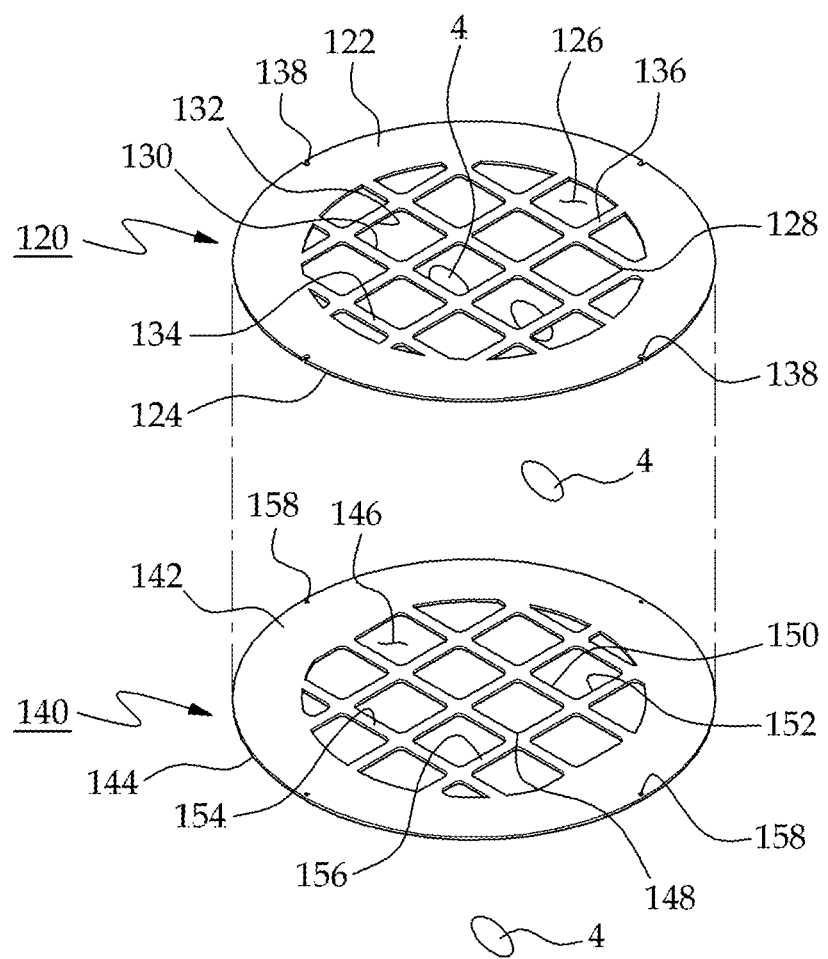

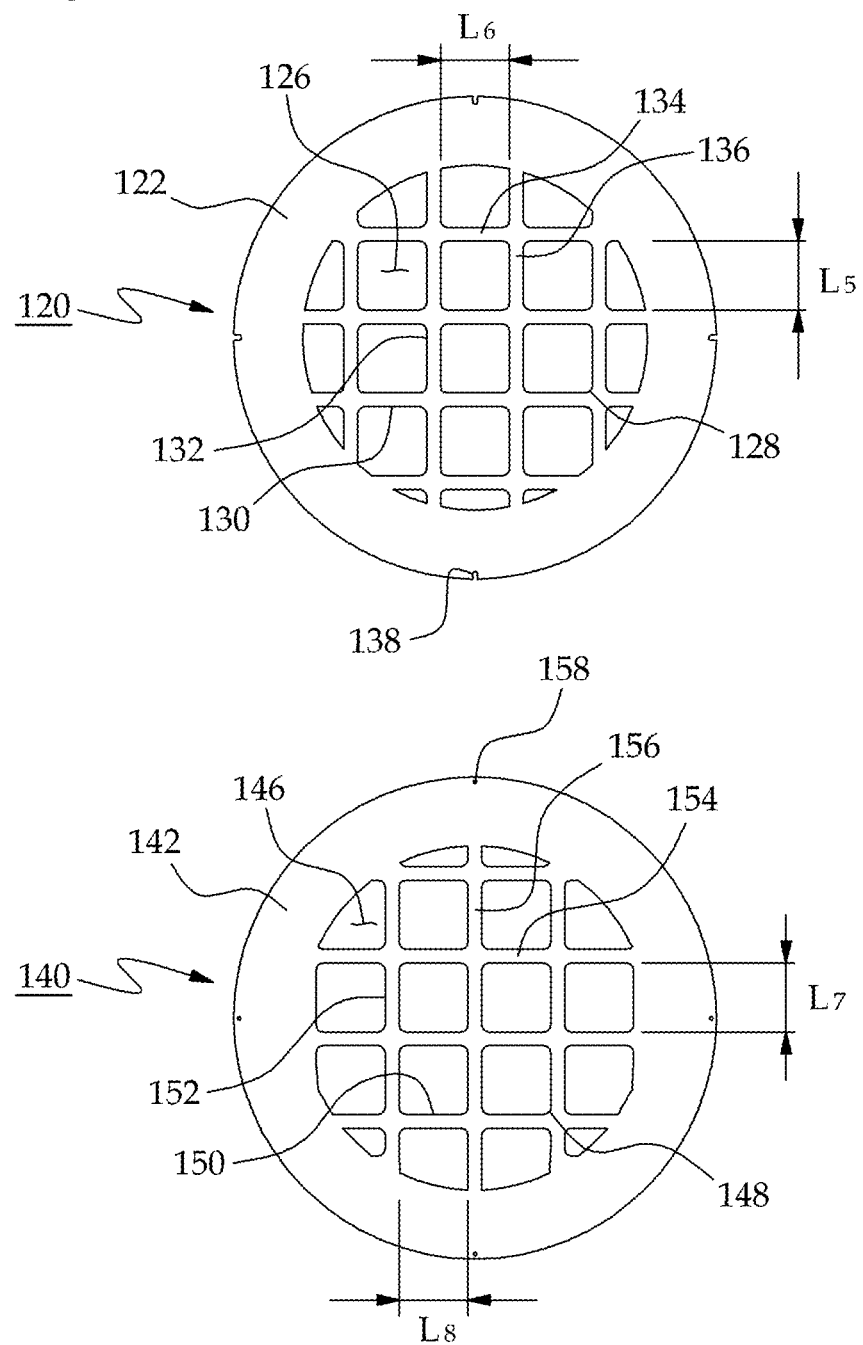
[Fig. 12]

[Fig. 13]
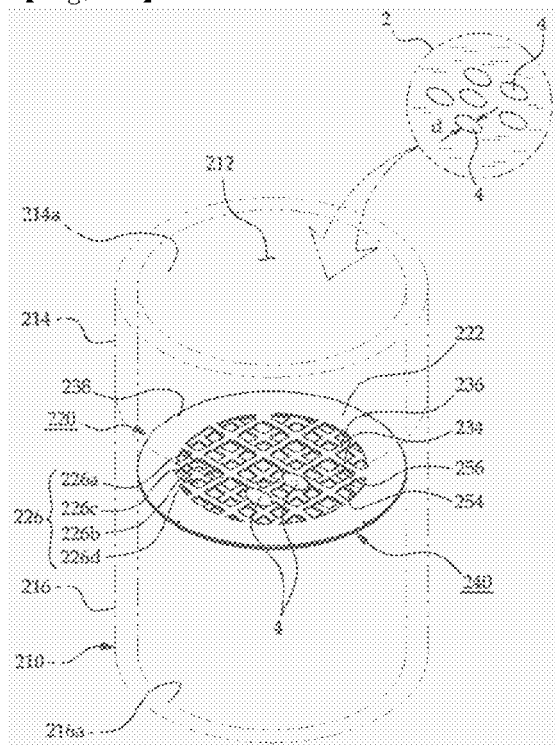
[Fig. 14]
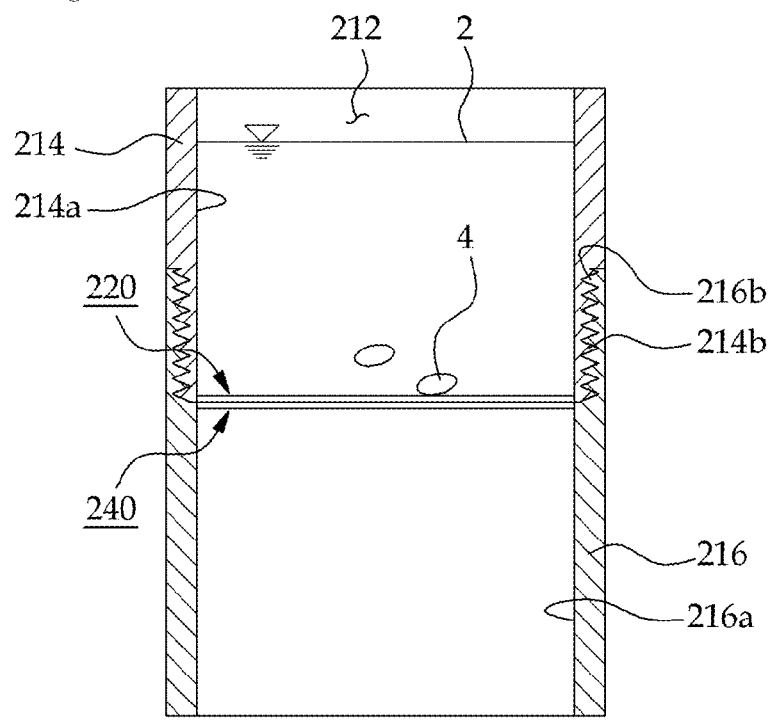

[Fig. 15]
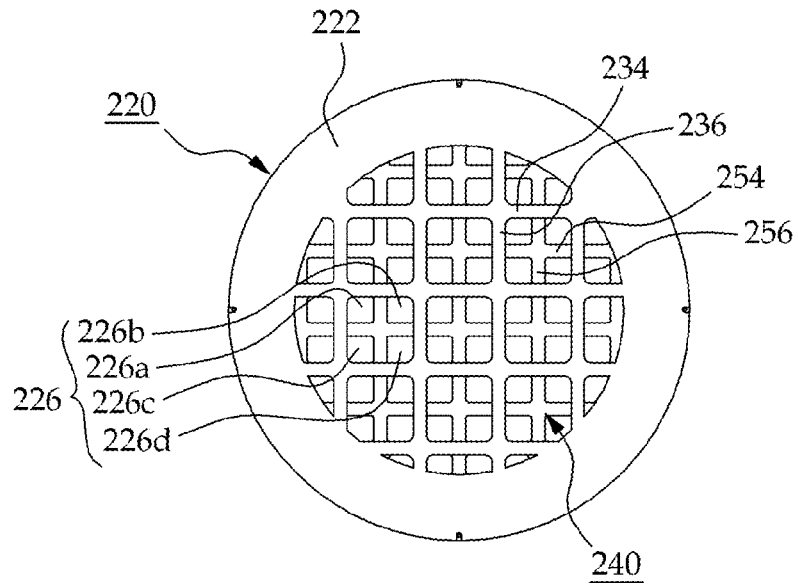
[Fig. 16]
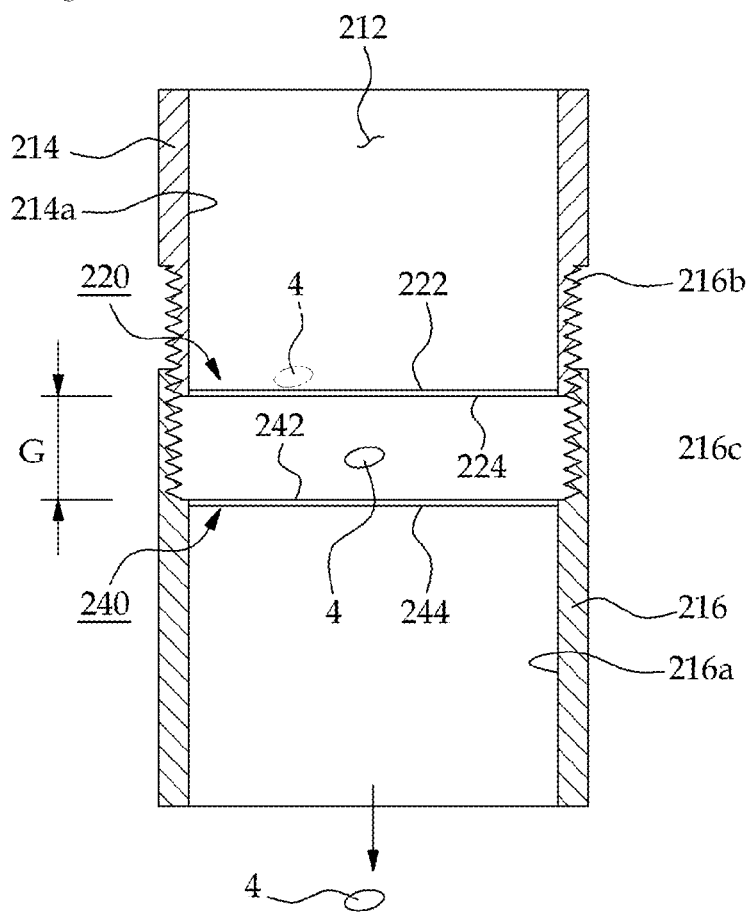

[Fig. 17]
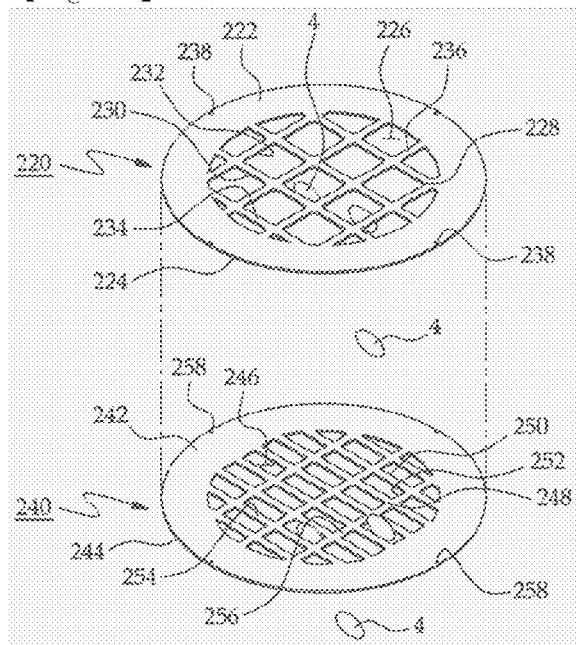
[Fig. 18]
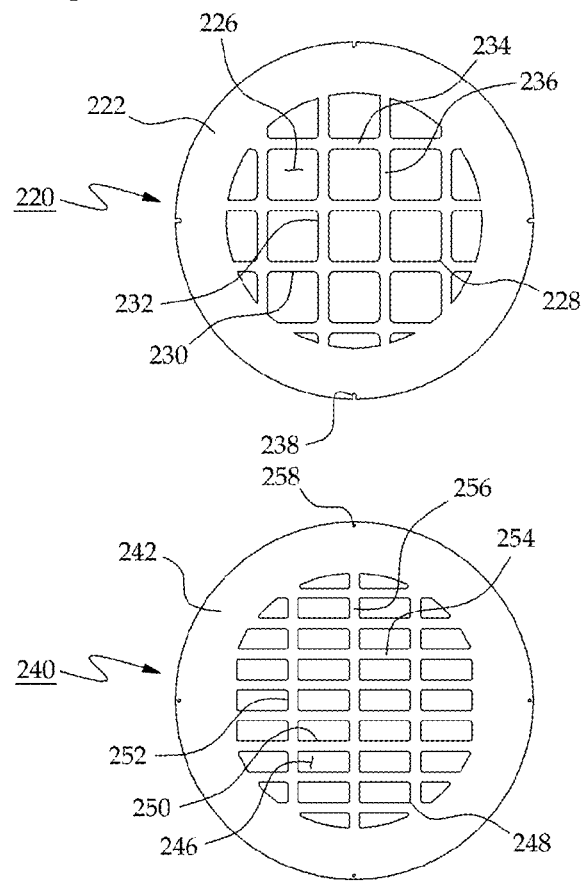

though the first pores; and a second filter having a plurality of second pores formed into a size that enables the target cells contained to pass through the second pores, the second filter arranged below the first filter in such a position as to filter the target cells.

The first filter and the second filter may be arranged such that the first pores and the second pores get out of alignment with each other. The first filter and the second filter may be arranged to move away from each other such that the target cells pass through the second pores.

Advantageous Effects of the Invention

The present cell collecting device is capable of separating target cells from a fluid sample such as blood or physiological fluid and easily and efficiently collecting the target cells. Accordingly, the present cell collecting device is useful in collecting target cells from the human blood for the purpose of analysis, inspection, drug trials and clinical tests.

BRIEF DESCRIPTION OF THE DRAWINGS

FIG. 1 is a perspective view showing the configuration of a cell collecting device according to a first embodiment of the present invention.

FIG. 2 is a section view of the cell collecting device of the first embodiment.

FIG. 3 is a plan view showing a first filter and a second filter of the cell collecting device of the first embodiment which are kept in an overlapping state.

FIG. 4 is a partially enlarged section view taken along line IV-IV in FIG. 3.

FIG. 5 is a perspective view showing the first filter and the second filter of the cell collecting device of the first embodiment which are kept in a spaced-apart state.

FIG. 6 is a plan view showing the first filter and the second filter of the cell collecting device of the first embodiment which are arranged side by side.

FIG. 7 is a perspective view showing the configuration of a cell collecting device according to a second embodiment of the present invention.

FIG. 8 is a section view of the cell collecting device of the second embodiment.

FIG. 9 is a plan view showing a first filter and a second filter of the cell collecting device of the second embodiment which are kept in an overlapping state.

FIG. 10 is a section view showing the first filter and the second filter of the cell collecting device of the second embodiment which are kept in a spaced-apart state.

FIG. 11 is a perspective view showing the first filter and the second filter of the cell collecting device of the second embodiment which are kept in a spaced-apart state.

FIG. 12 is a plan view showing the first filter and the second filter of the cell collecting device of the second embodiment which are arranged side by side.

FIG. 13 is a perspective view showing the configuration of a cell collecting device according to a third embodiment of the present invention.

FIG. 14 is a section view of the cell collecting device of the third embodiment.

FIG. 15 is a plan view showing a first filter and a third filter of the cell collecting device of the third embodiment which are kept in an overlapping state.

METHOD OF COLLECTING TARGET CELLS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to a cell collecting device and, more particularly, to a cell collecting device capable of filtering and collecting target cells from a fluid sample such as blood or physiological fluid.

BACKGROUND OF THE INVENTION

In recent years, regulations are increasingly strengthened on a biological test and a clinical test conducted for the sake of treatment of human diseases. As an alternative for the biological test and the clinical test, research and development have been extensively made on the collection of live cells from the human blood. The collection of cells is conducted by different kinds of cell collecting devices such as a micro-fluidic device, a CTC (Circulating Tumor Cell) chip, a filter, and so forth.

As one example of the cell collecting device, U.S. Patent Publication No. 2007/0025883A1 discloses a parylene membrane filter for filtering cells from fluid. The membrane filter is installed within a chamber and is provided with a plurality of pores formed to deter passage of cells, e.g., cancer cells.

As another example of the cell collecting device, U.S. Patent Publication No. 2009/0188864A1 discloses a method and apparatus for microfiltration to perform cell separation. A plurality of filter patches is installed in the central square hole of the microfiltration apparatus. Each of the filter patches is formed of a membrane having a plurality of pores for filtering cells. In the technologies of U.S. Patent Publication Nos. 2007/0025883A1 and 2009/0188864A1, the cancer cells filtered by the filter are recovered and collected by supplying a solution, e.g., water, into a chamber in a backward direction and forcibly discharging the cancer cells out of the chamber. This poses a problem in that it is quite difficult to recover and collect the cancer cells from the filter. Another problem lies in that the cancer cells are easily damaged in the process of discharging the cancer cells from the chamber.

SUMMARY OF THE INVENTION

Technical Problems

In view of the problems noted above, it is an object of the present invention to provide a cell collecting device capable of filtering and collecting target cells from a fluid sample such as blood or physiological fluid.

Another object of the present invention is to provide a cell collecting device capable of readily and efficiently discharging target cells captured by a screen filter, enhancing a collecting percentage of the target cells and preventing the target cells from being damaged.

Means for Solving the Problems

In order to achieve these objects, the present invention provides a cell collecting device, including: a first filter FIG. 16 is a section view showing the first filter and the third filter of the cell collecting device of the third embodiment which are kept in a spaced-apart state.

FIG. 17 is a perspective view showing the first filter and the third filter of the cell collecting device of the third embodiment which are kept in a spaced-apart state.

FIG. 18 is a plan view showing the first filter and the third filter of the cell collecting device of the third embodiment which are arranged side by side.

DETAILED DESCRIPTION OF EMBODIMENTS

Other objects, specific advantages and novel features of the present invention will become apparent from the following description of embodiments made in conjunction with the accompanying drawings.

Certain embodiments of a cell collecting device according to the present invention will now be described in detail with reference to the accompanying drawings.

A cell collecting device according to a first embodiment of the present invention is shown in FIGS. 1 through 6. Referring to FIGS. 1 and 2, the cell collecting device of the first embodiment is configured to capture target cells 4 contained in a fluid sample 2, thereby collecting the target cells 4. The target cells 4 have a diameter d.

The fluid sample 2 includes physiological fluid such as saliva, sweat or urine of a human or an animal, blood and serum. In addition, the fluid containing target cells 4 such as cells or tissues of a human, an animal or a plant and the fluid containing viruses or bacteria may be selected as the fluid sample 2. If the blood is selected as the fluid sample 2, the cells of different sizes contained in the blood may become the target cells 4. Examples of the cells contained in the blood include red blood cells, white blood cells and cancer cells. In the present embodiment, the white blood cells and the cancer cells may be selected as the target cells 4. The red blood cells may be selected as non-target cells.

The cell collecting device of the first embodiment includes a conduit 10 through which the fluid sample 2 can flow. The conduit 10 includes a passage 12 through which a large amount of fluid sample 2 containing target cells 4 can flow smoothly. The fluid sample 2 is supplied to the upstream end of the conduit 10 by a fluid sample supply means (not shown). Examples of the fluid sample supply means include a syringe, a blood collection tube, a bag, a pack or other containers capable of storing a specified amount of fluid sample and supplying the fluid sample to the upstream end of the conduit 10. The fluid sample supply means may be formed of a syringe pump or a plunger pump for pumping the fluid sample 2. While the passage 12 shown in FIG. 1 has a circular cross section, the present invention is not limited thereto. Alternatively, the passage 12 may be formed into a rectangular cross-sectional shape or other cross-sectional shapes.

Referring to FIGS. 1 through 6, the cell collecting device of the first embodiment further includes a first filter 20 installed in the passage 12 of the conduit 10. The first filter 20 includes a first front surface 22, a first rear surface 24 and a plurality of first pores 26. The first pores 26 are formed into such a size as to allow the target cells 4 to pass therethrough. Each of the first pores 26 has corner portions 28 formed into a round shape so as to prevent the target cells 4 from being damaged by the corner portions 28.

Each of the first pores 26 has a rectangular shape and includes a pair of first longitudinal sides 30 extending parallel to each other and a pair of first transverse sides 32 extending parallel to each other. The length $L_1$ of the first longitudinal sides 30 is larger than the length $L_2$ of the first transverse sides 32. The first filter 20 includes a plurality of first transverse strips 34 arranged between the first pores 26 to extend in a breadth-wise direction (X-axis direction) and a plurality of first longitudinal strips arranged between the first pores 26 to extend in a length-wise direction (Y-axis direction). The first transverse strips 34 and the first longitudinal strips 36 are formed to have the same width. The first transverse strips 34 and the first longitudinal strips 36 have a width smaller than the diameter d of the target cells 4. Four locating grooves 38 are formed at a regular interval along the outer peripheral edge of the first filter 20.

The cell collecting device of the first embodiment further includes a second filter 40 installed in the passage 12 of the conduit 10 and arranged below the first filter 20. The second filter 40 includes a second front surface 42, a second rear surface 44 and a plurality of second pores 46. Each of the second pores 46 has a rectangular shape and includes a pair of second longitudinal sides 50 extending parallel to each other and a pair of second transverse sides 52 extending parallel to each other. The second pores 46 are formed into such a size as to allow the target cells 4 to pass therethrough. Each of the second pores 46 has corner portions 48 formed into a round shape so as to prevent the target cells 4 from being damaged by the corner portions 48.

The length $L_3$ of the second longitudinal sides 50 is larger than the length $L_4$ of the second transverse sides 52. The second filter 40 includes a plurality of second transverse strips 54 arranged between the second pores 46 to extend in a breadth-wise direction (X-axis direction) and a plurality of second longitudinal strips 56 arranged between the second pores 46 to extend in a length-wise direction (Y-axis direction). The second transverse strips 54 and the second longitudinal strips 56 are formed to have the same width. Four locating projections 58 are formed at a regular interval along the outer peripheral edge of the second filter 40. If the locating projections 58 are brought into engagement with the locating grooves 38, the first filter 20 and the second filter 40 are accurately located in position with respect to each other.

As shown in FIGS. 1 and 2, the second filter 40 is installed in the passage 12 so as to move between a first position where the second front surface 42 comes into contact with the first rear surface 24 and a second position where the second front surface 42 stays spaced apart from the first rear surface 24. The first filter 20 and the second filter 40 are arranged such that the first pores 26 and the second pores 46 get out of alignment with each other when the first filter 20 and the second filter 40 are superimposed to have the second front surface 42 make contact with the first rear surface 24. The second front surface 42 is arranged just below the first pores 26 to partially close the first pores 26, thereby filtering the target cells 4. In other words, the second longitudinal strips 56 are arranged across the central regions of the first pores 26 so as to partially close the first pores 26 at the lower side of the first pores 26. If the second longitudinal strips 56 are arranged across the central regions of the first pores 26 in this manner, each of the first pores 26 is divided by each of the second longitudinal strips 56 into two split holes 26$a$ and 26$b$ having a size small enough to deter passage of the target cells 4. While the first filter 20 and the second filter 40 are superimposed so as to filter the target cells 4 in the present embodiment, the present invention is not limited thereto. Alternatively, the second filter 40 may be arranged in a spaced-apart relationship with the first filter 20 so that the target cells 4 cannot pass through between the first rear surface 24 and the second front surface 42.

As indicated by a double-dot chain line in FIG. 2, if the second filter 40 is moved away from the first filter 20 such that a gap G exists between the first rear surface 24 and the second front surface 42, the target cells 4 are allowed to smoothly pass through between the first filter 20 and the second filter 40. At this time, the gap G is set larger than the diameter d of the target cells 4. While the second filter 40 is installed in the passage 12 so as to move with respect to the first filter 20 in the present embodiment, the present invention is not limited thereto. Alternatively, the first filter 20 may be installed in the passage 12 so as to move with respect to the second filter 40.

The first filter 20 and the second filter 40 are made of, e.g., stainless steel, nickel, aluminum or parylene. The first pores 26 and the second pores 46 are formed into a micrometer size so as to filter the target cells 4, e.g., cancer cells. The first pores 26 and the second pores 46 having a micrometer size can be formed by etching or electroforming through the use of a MEMS (Micro-Electro-Mechanical System) technology. The first filter 20 and the second filter 40 are rigid enough not to be deformed by the pressure of the fluid sample 2 or a solution flowing through the passage 12.

Next, description will be made on the operation of the cell collecting device of the first embodiment configured as above.

Referring to FIGS. 1, 2 and 4, if the fluid sample 2 is supplied to the upstream end of the conduit 10 in a state that the second filter 40 is superimposed on the first filter 20 such that the first pores 26 and the second pores 46 get out of alignment with each other, the target cells 4 contained in the fluid sample 2 flowing along the passage 12 are obstructed by the first transverse strips 34, the first longitudinal strips 36 and the second longitudinal strips 56. Thus, the target cells 4 cannot pass through the split holes 26a and 26b. The first transverse strips 34 and the first longitudinal strips 36 have a width smaller than the diameter d of the target cells 4. Accordingly, the target cells 4 cannot stay on the first transverse strips 34 and the first longitudinal strips 36 and flows into the first pores 26.

The non-target cells contained in the fluid sample 2 are moved through the split holes 26a and 26b and then discharged out of the conduit 10. Red blood cells as one example of the non-target cells are easily deformable and, therefore, can smoothly pass through the split holes 26a and 26b. Moreover, the red blood cells cannot stay on the first transverse strips 34, the first longitudinal strips 36 and the second longitudinal strips 56.

Referring to FIGS. 2 and 5, the second filter 40 is moved away from the first filter 20 along the flow direction of the fluid sample 2 and is spaced apart from the first filter 20 after the fluid sample 2 is completely discharged out of the conduit 10. In this case, the target cells 4 are moved through the first pores 26 and the second pores 46 and are then discharged out of the conduit 10. At this time, carrier fluid, e.g., a solution may be supplied to the upstream end of the conduit 10 in order to assure smooth movement of the target cells 4. The target cells 4 discharged out of the conduit 10 can be received in a container, e.g., a test tube or a culture dish. In this manner, the target cells 4 such as live white blood cells or cancer cells can be efficiently separated and collected from the human blood through the combined use of the first filter 20 and the second filter 40.

FIGS. 7 through 12 show a cell collecting device according to a second embodiment of the present invention. Referring to FIGS. 7, 8 and 10, the cell collecting device of the second embodiment includes a conduit 110 defining a passage 112 through which the fluid sample 2 can pass. The conduit 110 is divided into an upper conduit part or a first tube 114 having an upper passage 114a and a lower conduit part or a second tube 116 having a lower passage 116a.

The upper passage 114a of the upper conduit part 114 and the lower passage 116a of the lower conduit part 116 are interconnected so as to define the passage 112. The lower conduit part 116 includes a step 116b formed in the inner surface thereof and a counterbore 116c extending upward from the step 116b. The lower portion of the upper conduit part 114 is fitted to the counterbore 116c with the lower end thereof supported on the step 116b.

Referring to FIGS. 7 through 12, the cell collecting device of the second embodiment includes a first filter 120 installed in the lower portion of the upper passage 114a. The first filter 120 includes a first front surface 122, a first rear surface 124, a plurality of first pores 126 and four locating grooves 138. The first pores 126 are formed to have a cross-sectional area large enough to allow the target cells 4 to pass through the first pores 126. Each of the first pores 126 includes corner portions 128 formed into a round shape. Each of the first pores 126 has a substantially rectangular shape and includes a pair of first transverse sides 130 extending parallel to each other and a pair of first longitudinal sides 132 extending parallel to each other. The length $L_5$ of the first transverse sides 130 is equal to the length $L_6$ of the first longitudinal sides 132. The first filter 120 includes a plurality of first transverse strips 134 and a plurality of first longitudinal strips 136 intersecting the first transverse strips 134. The first transverse strips 134 and the first longitudinal strips 136 are formed to have the same width.

The cell collecting device of the second embodiment further includes a second filter 140 installed in the upper portion of the lower passage 116a. The second filter 140 includes a second front surface 142, a second rear surface 144, a plurality of second pores 146 and four locating projections 158. Each of the second pores 146 has a substantially square shape and includes round corner portions 148, a pair of second transverse sides 150 and a pair of second longitudinal sides 152. The length $L_7$ of the second transverse sides 150 is equal to the length $L_8$ of the second longitudinal sides 152. The second filter 140 includes a plurality of second transverse strips 154 and a plurality of second longitudinal strips 156 intersecting the second transverse strips 154. The second transverse strips 154 and the second longitudinal strips 156 are formed to have the same width.

Referring to FIGS. 7 through 9, if the lower portion of the upper conduit part 114 is fitted to the counterbore 116c of the lower conduit part 116 and if the lower end of the upper conduit part 114 is supported on the step 116b, the first rear surface 124 of the first filter 120 comes into contact with the second front surface 142 of the second filter 140. If the first filter 120 and the second filter 140 are superimposed each other, the second transverse strips 154 and the second longitudinal strips 156 are arranged at the centers of the first pores 126. Each of the first pores 126 is divided by the second transverse strips 154 and the second longitudinal strips 156 into four split holes 126a, 126b, 126c and 126d having a size small enough to deter passage of the target cells 4.

If the fluid sample 2 is supplied to the upstream end of the upper conduit part 114 as shown in FIGS. 7 and 8, the target cells 4 contained in the fluid sample 2 flowing along the passage 112 are obstructed by the first transverse strips 134, the first longitudinal strips 136, the second transverse strips 154 and the second longitudinal strips 156 and cannot pass through the split holes 126a, 126b, 126c and 126d. Non-target cells are moved through the split holes 126*a*, 126*b*, 126*c* and 126*d* and are then discharged out of the conduit 110.

Referring to FIGS. 10 and 11, if the flow sample 2 is completely discharged, the upper conduit part 114 is moved away from the lower conduit part 116 so that the first filter 120 and the second filter 140 can be spaced apart from each other. Along with the movement of the upper conduit part 114, the first filter 120 and the second filter 140 are spaced apart from each other, thereby creating a gap G between the first rear surface 124 and the second front surface 142 so that the target cells 4 can pass through the first filter 120 and the second filter 140. After passing through the first pores 126 and the second pores 146, the target cells 4 are moved along the passage 112 and then discharged out of the conduit 110. In the present embodiment, the gap G existing between the first filter 120 and the second filter 140 may be created by moving the lower conduit part 116 downward away from the upper conduit part 114.

FIGS. 13 through 18 show a cell collecting device according to a third embodiment of the present invention. Referring to FIGS. 13, 14 and 16, the cell collecting device of the third embodiment includes a conduit 210 defining a passage 212 through which the fluid sample 2 can pass. The conduit 210 is divided into an upper conduit part 214 having an upper passage 214*a* and a lower conduit part 216 having a lower passage 216*a*.

The upper passage 214*a* of the upper conduit part 214 and the lower passage 216*a* of the lower conduit part 216 are interconnected so as to define the passage 212. The upper conduit part 214 includes a male thread portion 214*b* formed on the lower outer surface thereof. The lower conduit part 116 includes a female thread portion 216*b* formed on the upper inner surface thereof. The upper conduit part 214 and the lower conduit part 216 are removably combined together by coupling the male thread portion 214*b* and the female thread portion 216*b* with each other.

Referring to FIGS. 13 through 18, the cell collecting device of the third embodiment includes a first filter 220 installed in the lower portion of the upper passage 214*a*. The first filter 220 includes a first front surface 222, a first rear surface 224, a plurality of first pores 226 and four locating grooves 238. Each of the first pores 226 includes round corner portions 228, a pair of first transverse sides 230 and a pair of first longitudinal sides 232. The first filter 220 includes a plurality of first transverse strips 234 and a plurality of first longitudinal strips 236 intersecting the first transverse strips 234. The first filter 220 of the present embodiment is identical in configuration and operation with the first filter 120 of the second embodiment described above. Therefore, no detailed description will be made on the first filter 220.

The cell collecting device of the third embodiment further includes a second filter 240 installed in the upper portion of the lower passage 216*a*. The second filter 240 includes a second front surface 242, a second rear surface 244, a plurality of second pores 246 and four locating projections 258. Each of the second pores 246 includes round corner portions 248, a pair of second transverse sides 250 and a pair of second longitudinal sides 252. The second filter 240 includes a plurality of second transverse strips 254 and a plurality of second longitudinal strips 256 intersecting the second transverse strips 254. The second filter 240 of the present embodiment is identical in configuration and operation with the second filter 40 of the first embodiment described above. Therefore, no detailed description will be made on the second filter 240.

Referring to FIGS. 13 through 15, if the first filter 220 and the second filter 240 are superimposed each other so that the first rear surface 224 can make contact with the second front surface 242, the second transverse strips 254 and the second longitudinal strips 256 are arranged at the centers of the first pores 226. Each of the first pores 226 is divided by the second transverse strips 254 and the second longitudinal strips 256 into four split holes 226*a*, 226*b*, 226*c* and 226*d* having a size small enough to deter passage of the target cells 4.

In the cell collecting device of the third embodiment, if the male thread portion 214*b* is completely tightened to the female thread portion 216*b*, the second front surface 242 of the second filter 240 comes into contact with the first rear surface 224 of the first filter 220. If the fluid sample 2 is supplied to the upstream end of the upper conduit part 214, the target cells 4 contained in the fluid sample 2 flowing along the passage 212 are obstructed by the first transverse strips 234, the first longitudinal strips 236, the second transverse strips 254 and the second longitudinal strips 256 and cannot pass through the split holes 226*a*, 226*b*, 226*c* and 226*d*. Non-target cells are moved through the split holes 226*a*, 226*b*, 226*c* and 226*d* and are then discharged out of the conduit 210.

Referring to FIGS. 16 and 17, if the flow sample 2 is completely discharged, the male thread portion 214*b* and the female thread portion 216*b* are loosened by rotating one of the upper conduit part 214 and the lower conduit part 216, e.g., the upper conduit part 214. If the upper conduit part 214 is moved upward away from the lower conduit part 216, the first filter 220 and the second filter 240 are spaced apart from each other, thereby creating a gap G between the first rear surface 224 and the second front surface 242 so that the target cells 4 can pass through the first filter 220 and the second filter 240. After passing through the first pores 226 and the second pores 246, the target cells 4 are moved along the passage 212 and then discharged out of the conduit 210.

While the first pores 26, 126 and 226 and the second pores 46, 146 and 246 have a rectangular cross-sectional shape in the cell collecting device of the first through third embodiments, the present invention is not limited thereto. Alternatively, the cross-sectional shape of the first pores 26, 126 and 226 and the second pores 46, 146 and 246 may be changed to circular shape, an elliptical shape or other shapes. The cross-sectional shape of the first pores 26, 126 and 226 and the second pores 46, 146 and 246 is not particularly limited as long as the second front surfaces 42, 142 and 242 can at least partially close the first pores 26, 126 and 226 so as to filter the target cells 4 when the first filters 20, 120 and 220 and the second filters 40, 140 and 240 are superimposed each other and as long as the target cells 4 staying in the first pores 26, 126 and 226 can pass through the first pores 26, 126 and 226 and the second pores 46, 146 and 246 when the first filters 20, 120 and 220 and the second filters 40, 140 and 240 are spaced apart from each other. The size, position and interval of the first pores 26, 126 and 226 and the second pores 46, 146 and 246 may be appropriately changed depending on the kind of the target cells 4. The position and interval of the first pores 26, 126 and 226 and the second pores 46, 146 and 246 may be irregular.

While certain embodiments of the invention have been described above, the scope of the present invention is not limited to these embodiments. It will be apparent to those skilled in the art that various changes, modifications and substitutions may be made without departing from the scope of the invention defined in the claims. Such changes, modifications and substitutions shall be construed to fall within the scope of the present invention.

What is claimed is:

1. A method of collecting target cells, the method comprising:
   providing a cell collection device comprising a conduit defining a fluid channel, a first screen defining pores and a second screen defining second pores, the pores of the first screen comprising a first pore, the pores of the second screen comprising a second pore, the first and second screens being arranged in the fluid channel such that liquid flowing through the fluid channel in a flow direction passes the first screen first and the second screen second,
   wherein the first and second screens are movable relative to each other along the flow direction between a first configuration and a second configuration of the cell collection device, wherein in the first configuration, the first and second screens are at a first distance therebetween in the flow direction whereas in the second configuration, the first and second screens are at a second distance therebetween in the flow direction that is larger than the first distance,
   wherein in the first configuration, the first and second screens in combination form a combined filter, in which the first pore of the first screen and the second pore of the second screen are partially overlapping when viewed in the flow direction such that the combined filter is configured to screen target cells that would pass the first screen and the second screen individually, whereas in the second configuration, each of the first and second screens is to act independently;
   flowing a fluid composition comprising the target cells from a first end of the fluid channel toward a second end of the fluid channel in the flow direction while the cell collection device is in the first configuration, and screening at least part of the target cells by the combined filter and allowing at least part of the rest of the fluid composition to pass through the combined filter toward the second end of the fluid channel;
   subsequently, moving the first screen relative to the second screen along the flow direction from the first configuration to form the second configuration, to permit at least part of the target cells screened by the combined filter in the first configuration to pass the first screen first and then the second screen in the flow direction; and
   collecting at least part of the target cells at the second end of the fluid channel,
   wherein the conduit comprises a first tube and a second tube that are arranged along the flow direction, wherein the first screen is attached to the first tube, and the second screen is attached to the second tube.

2. The method of claim 1, wherein the first screen is attached to an end of the first tube, wherein the end of the first tube and the first screen are inserted into the second tube and configured to move relative to the second tube along the flow direction.

3. The method of claim 1, wherein each of the first and second tubes comprises a threaded wall, wherein the threaded wall of the first tube is engaged with the threaded wall of the second tube such that the first and second tubes can move relative to each other in the flow direction.

4. The method of claim 1, wherein at least part of the pores of the first screen is in a rectangular shape, wherein at least part of the pores of the second screen is in a rectangular shape.

5. The method of claim 1, wherein in the first configuration, the first screen and the second screen are in contact with each other.

6. The method of claim 1, wherein the fluid composition further comprises non-target cells that can pass through the combined filter.

7. The method of claim 6, wherein the fluid composition comprises human blood containing the target cells.

8. The method of claim 7, wherein the target cells comprise at least one of white blood cells and cancer cells.

9. The method of claim 7, wherein the pores of the first and second screens are sized and arranged to form the combined filter configured to screen at least one of white blood cells and cancer cells.

10. The method of claim 9, wherein the pores of the first and second screens are sized and arranged to form the combined filter configured to pass red blood cells therethrough.

* * * * *